(12) United States Patent
Quistgaard

(10) Patent No.: US 8,512,250 B2
(45) Date of Patent: Aug. 20, 2013

(54) COMPONENT ULTRASOUND TRANSDUCER

(75) Inventor: Jens U. Quistgaard, Seattle, WA (US)

(73) Assignee: Liposonix, Inc., Hayward, CA (US)

( * ) Notice: Subject to any disclaimer, the term of this patent is extended or adjusted under 35 U.S.C. 154(b) by 865 days.

(21) Appl. No.: 12/111,327

(22) Filed: Apr. 29, 2008

(65) Prior Publication Data

US 2008/0200813 A1   Aug. 21, 2008

Related U.S. Application Data

(62) Division of application No. 11/027,919, filed on Dec. 29, 2004.

(60) Provisional application No. 60/534,034, filed on Dec. 30, 2003.

(51) Int. Cl.
*A61B 8/14* (2006.01)

(52) U.S. Cl.
USPC .............. 600/459; 600/407; 600/437; 604/19

(58) Field of Classification Search
None
See application file for complete search history.

(56) References Cited

U.S. PATENT DOCUMENTS

| | | | |
|---|---|---|---|
| 4,913,157 A * | 4/1990 | Pratt et al. .................. | 600/449 |
| 5,076,276 A | 12/1991 | Sakurai et al. | |
| 5,143,063 A | 9/1992 | Fellner | |
| 5,151,085 A | 9/1992 | Sakurai et al. | |
| 5,163,433 A | 11/1992 | Kagawa et al. | |
| 5,219,401 A * | 6/1993 | Cathignol et al. ........... | 600/439 |
| 5,391,144 A | 2/1995 | Sakurai et al. | |
| 5,419,761 A | 5/1995 | Narayanan et al. | |
| 5,526,815 A | 6/1996 | Granz et al. | |
| 5,594,165 A * | 1/1997 | Madanshetty .............. | 73/61.75 |
| 5,618,275 A | 4/1997 | Bock | |
| 5,687,717 A | 11/1997 | Halpern et al. | |
| 5,688,235 A | 11/1997 | Sakurai et al. | |
| 5,769,790 A | 6/1998 | Watkins et al. | |
| 5,800,365 A * | 9/1998 | Zhong et al. ..................... | 601/4 |
| 5,827,204 A | 10/1998 | Grandia et al. | |
| 5,836,897 A | 11/1998 | Sakurai et al. | |
| 5,928,169 A | 7/1999 | Schatzle et al. | |
| 5,931,836 A | 8/1999 | Hatta et al. | |

(Continued)

FOREIGN PATENT DOCUMENTS

| WO | WO 93/01752 | 2/1993 |
|---|---|---|
| WO | WO 00/36982 | 6/2000 |
| WO | WO 02/054018 A2 | 7/2002 |

OTHER PUBLICATIONS

Candian Intellectual Property Office, Office Action received in related Canadian patent application No. 2,551,325 dated Sep. 5, 2012.

(Continued)

*Primary Examiner* — Unsu Jung
*Assistant Examiner* — Nasir S Shahrestani
(74) *Attorney, Agent, or Firm* — Wood, Herron & Evans, LLP

(57) ABSTRACT

An ultrasound transducer having multiple focal zones is described. In one embodiment there is an ultrasound transducer manufactured as a single piece but having two or more focal zones. In a second embodiment there is a transducer assembly combining a high frequency and low frequency transducer. In a third embodiment there is an interchangeable assembly allowing for different ultrasound transducers to be used based on procedural needs. Variations of each embodiment are also disclosed.

8 Claims, 5 Drawing Sheets

(56) References Cited

U.S. PATENT DOCUMENTS

| | | | |
|---|---|---|---|
| 6,019,775 | A | 2/2000 | Sakurai et al. |
| 6,039,048 | A | 3/2000 | Sillberg |
| 6,056,735 | A | 5/2000 | Okada et al. |
| 6,071,239 | A | 6/2000 | Cribbs et al. |
| 6,113,558 | A | 9/2000 | Rosenschein et al. |
| 6,241,753 | B1 | 6/2001 | Knowlton |
| 6,266,551 | B1 | 7/2001 | Osadchy et al. |
| 6,309,355 | B1* | 10/2001 | Cain et al. .............. 600/439 |
| 6,325,769 | B1 | 12/2001 | Klopotek |
| 6,340,352 | B1 | 1/2002 | Okada et al. |
| 6,350,245 | B1 | 2/2002 | Cimino |
| 6,387,380 | B1 | 5/2002 | Knowlton |
| 6,425,867 | B1 | 7/2002 | Vaezy et al. |
| 6,500,126 | B1 | 12/2002 | Brock-Fisher |
| 6,511,428 | B1* | 1/2003 | Azuma et al. ............ 600/439 |
| 6,607,498 | B2 | 8/2003 | Eshel |
| 6,613,005 | B1 | 9/2003 | Friedman et al. |
| 6,623,423 | B2 | 9/2003 | Ozaki et al. |
| 6,629,928 | B1 | 10/2003 | Dolan et al. |
| 6,660,002 | B1 | 12/2003 | Edwards et al. |
| 6,679,875 | B2 | 1/2004 | Honda et al. |
| 6,761,698 | B2 | 7/2004 | Shibata et al. |
| 7,063,692 | B2 | 6/2006 | Sakurai et al. |
| 7,296,318 | B2* | 11/2007 | Mourad et al. ............. 15/22.1 |
| 8,282,554 | B2 | 10/2012 | Makin et al. |
| 2002/0107538 | A1 | 8/2002 | Shibata et al. |
| 2002/0128592 | A1 | 9/2002 | Eshel |
| 2003/0074010 | A1* | 4/2003 | Taleyarkhan ............. 606/128 |
| 2003/0076591 | A1 | 4/2003 | Ohmori et al. |
| 2003/0088185 | A1 | 5/2003 | Prass |
| 2005/0027195 | A1 | 2/2005 | Govari |
| 2005/0101945 | A1 | 5/2005 | Sakurai et al. |
| 2005/0154308 | A1 | 7/2005 | Quistgaard et al. |
| 2005/0154309 | A1 | 7/2005 | Etchells et al. |
| 2005/0154431 | A1 | 7/2005 | Quistgaard et al. |
| 2005/0187463 | A1 | 8/2005 | Quistgaard et al. |
| 2005/0187495 | A1 | 8/2005 | Quistgaard et al. |
| 2005/0193451 | A1 | 9/2005 | Quistgaard et al. |
| 2007/0055156 | A1 | 3/2007 | Desilets et al. |
| 2008/0091104 | A1* | 4/2008 | Abraham .................. 600/439 |

OTHER PUBLICATIONS

USPTO, Office Action issued in related U.S. Appl. No. 11/027,919 dated Sep. 20, 2012.

USPTO, Office Action issued in U.S. Appl. No. 11/027,919 dated Apr. 25, 2013.

* cited by examiner

COMPONENT ULTRASOUND TRANSDUCER

CROSS-REFERENCES TO RELATED APPLICATIONS

This application is a divisional of U.S. application Ser. No. 11/027,919, filed Dec. 29, 2004, which claims the benefit of provisional application No. 60/534,034, filed on Dec. 30, 2003, the full disclosures of which are incorporated herein by reference.

The subject matter of the present application is related to that of the following applications: Ser. No. 10/750,370, entitled "Medical Device Inline Degasser"; Ser. No. 10/751,344, entitled "Articulating Arm for Medical Procedures"; Ser. No. 10/750,369, entitled "Disposable Transducer Seal"; 60/533,528, entitled "Position Tracking Device"; 60/533,988, entitled "Method for Planning and Performing Ultrasound Therapy"; 60/534,036, entitled "Ultrasound Therapy with Hood Movement Control"; and 60/533,958, entitled "Systems and Methods for the Destruction of Adipose Tissue"; the full disclosure of each of these applications are incorporated herein by reference.

BACKGROUND OF THE INVENTION

1. Field of the Invention

The present invention relates to ultrasound transducers devices for the destruction of adipose tissue through the projection of ultrasound energy into adipose tissue without an invasive component. In particular this invention details transducers having multiple focal points, or devices using multiple transducers to perform non-invasive adipose tissue destruction.

2. Description of the Prior Art

Body sculpting has developed into a highly sought after procedure for reducing a person's weight and restoring people to a leaner, trimmer physique. The field of cosmetic surgery has ballooned considerably with developments in both tools and techniques. One of the more popular for both quick weight loss and body sculpting is liposuction.

Liposuction is a method of body contouring that can dramatically improve the shape and contour of different body areas by sculpting and removing unwanted fat. More than 200,000 liposuction procedures are performed annually. Recent innovations and advances in the field of liposuction include the tumescent technique and an ultrasonic assisted technique. Traditional liposuction was done by making small incisions in desired locations, then inserting a hollow tube or cannula under the skin in the fat layer. The cannula is connected to a vacuum and the fat is vacuumed out under high suction pressure. This procedure indiscriminately removed fat, connective tissue, blood vessels and nerve tissue. The procedure caused bleeding, bruising, trauma, and blood loss, restricting the amount of fat removal possible.

The Tumescent technique allows for removal of significantly more fat during the operation with less blood loss. Tumescent liposuction injects a fat layer with large amounts of saline and adrenalin solution before suctioning. A cannula is again used with a suction device to remove fat. This procedure reduces the bleeding of traditional liposuction. However the procedure still removes a significant amount of structural tissue, blood and nerve endings.

The most recently approved innovation is Ultrasound Assisted Lipoplasty (UAL). UAL utilizes a titanium cannula that has the tip vibrating at ultrasound frequency. This vibration disrupts the near volume fat cells and essentially liquefies them for easy removal. UAL uses a low power suction and draws the fat material only in the near vicinity of the cannula tip. This technique is more refined and gentle to the tissues, there is less blood loss, less bruising, less pain, and a significantly faster recovery.

The use of ultrasound for surgical procedure is not restricted to UAL. High intensity focused ultrasound (HIFU) techniques have been employed by others for cancer therapy.

U.S. Pat. No. 6,309,355 to Cain et al., discloses a method of generating micro-bubbles in a target tissue and then using an ultrasound source to cause the micro bubbles to create a cavitation effect to destroy nearby tissue. The preferred embodiment utilizes a low frequency ultrasound source (less than 500 kHz) to cause the cavitation. A diagnostic instrument is used to determine the location of the individual surgical lesions.

PCT application WO 02/054018 A2 to Eshel, et al., provides for a method of lysing adipose tissue in a region of the human body while simultaneously not lysing non-adipose tissue. The method describes the use of HIFU in the body coupled to a diagnostic imaging system and a computer to track the areas being irradiated with HIFU energy.

The following additional references are relevant in the art: U.S. Pat. Nos. 5,769,790; 6,113,558; 5,827,204; 5,143,063; 5,219,401; 5,419,761; 5,618,275; 6,039,048; 6,425,867; 5,928,169; 6,387,380; 6,350,245; 6,241,753; 5,526,815; 6,071,239; 5,143,063; and WO 00/36982

Current methods for using High Intensity Focused Ultrasound (HIFU) to form lesions in biologic tissues via cavitation effects suffer from a variety of practical limitations. In order to reach the intensities necessary for cavitation, previous work has typically involved use of physically large (i.e. of diameters greater than 2 cm, typically in the range of 5 to 10 cm) focused transducers at relatively low (i.e. less than 1.5 MHz) frequencies and fairly high (i.e. greater than 50 Watts) output energy. Large transducers and high power levels are typically required at low frequencies in order to reach local intensities at the transducer focal point of a magnitude sufficient for cavitation. Low frequencies, even approaching sonic frequencies (i.e. 20 KHz) may be preferred for cavitation effects. A physically large transducer practically limits clinical applications for several reasons.

Physical contact must typically be maintained between the entire active surface of a large transducer and a patient. This contact is often maintained through a coupling material in order to properly transmit the ultrasound energy into the target tissue. Larger transducers are more difficult to keep properly coupled due to natural contours of tissue. Ideally, there should be no intervening media between the transducer and the focal volume where the lesion is to be formed that pose large discontinuities in acoustic properties (thus causing reflections, refraction, and the like). Larger transducers are more difficult to position so that the entire aperture is clear of intervening media such as bone or gas pockets that may degrade or destroy the ability to focus properly. Furthermore, large transducers with very shallow focal depths are difficult, if not impossible to manufacture and apply properly. Typical ratios of focal depth to aperture size are not less than 1 (an f/1 design). Even if this ratio can be physically decreased, acoustic coupling becomes problematic due to critical angle effects. A standoff can be used to physically move the transducer away from the target tissue while maintaining coupling, but this has drawbacks in terms of increased intensity at the tissue surface, and simply being physically unwieldy.

In addition, the focal point of each transducer is at a fixed depth below the skin surface and the destruction of adipose tissue using a fixed focal length transducer cannot be adjusted by a user. Transducers are manufactured with specific frequencies, amplitudes, focal depths and power capabilities and these variables cannot be altered after the manufacturing process is complete. The result is that procedures which attempt to utilize high intensity focused ultrasound to produce adipose tissue destruction through heating, cavitation or some combination of the two, are restricted to operate at a particular tissue depth, and are unable to make even slight adjustments to the transducer parameters except to completely change transducers. Thus if a patient wishes to have a volume of adipose tissue treated that is large, such that a liposuction procedure would normally be called for, a high intensity focused ultrasound device would not be able to handle the depths and breadths as variables to the operation. Thus high intensity focused ultrasound procedure is still not a better option for the patient since the result is restricted to a thin layer of adipose tissue at a fixed depth below the surface of the skin.

Although liposuction procedures have been refined, and non invasive techniques and devices are in development, there is still a need for an ultrasound transducer that can produce the desired lesion formation to maximize effective lipolysis treatment in a short exposure time.

There is further a need for a transducer having an adaptive ability to conform to different procedural requirements involving changes in frequency, power output, and activation time.

There is still further a need for a transducer device capable of delivering high intensity focused ultrasound to a patient without causing producing skin burns.

BRIEF SUMMARY OF THE INVENTION

Therefore it is an object of the present invention to provide a transducer capable of transmitting high intensity ultrasound energy into two or more focal zones simultaneously.

It is another object of the present invention to provide for a transducer capable of focusing two or more different frequencies into a single focal zone, or into a group of focal zones.

Another object of the present invention is to provide an adaptive transducer device capable of responding to the demands of different treatment requirements.

It is still further an objective of the present invention to provide for a transducer that will eliminate the danger of skin burns on the epidermis of a patient undergoing a lipolysis treatment.

At least one of these objectives is realized in an ultrasound transducer split into two or more equal size sections wherein each section has a discrete focal point.

In another embodiment of the present invention is a transducer assembly comprising a first focused ultrasound transducer operating at a high frequency for causing bubble formation in adipose tissue and a second transducer operating at a low frequency for collapsing the bubbles formed by the first transducer.

Still another embodiment there is an interchangeable electronic medical instrument assembly comprising a receptacle having a plurality of sockets. There is a plurality of electronic medical instruments having a common style electronic communication plug for engaging the plurality of sockets. The plurality of electronic medical instruments each have an electronic identity. A medical appliance is operationally connected to the receptacle and has at least one signal generator, a data I/O bus, and a power supply wherein the medical appliance can detect and identify each electronic medical instrument through the electronic communication plug when the plugs are engaged in the sockets. The medical appliance can control each of the electronic medical instruments according to a set of operation parameters.

The electronic medical devices may be ultrasound transducers, sensors, or other electronically controllable medical devices.

DETAILED DESCRIPTION OF THE INVENTION

Figure 1:
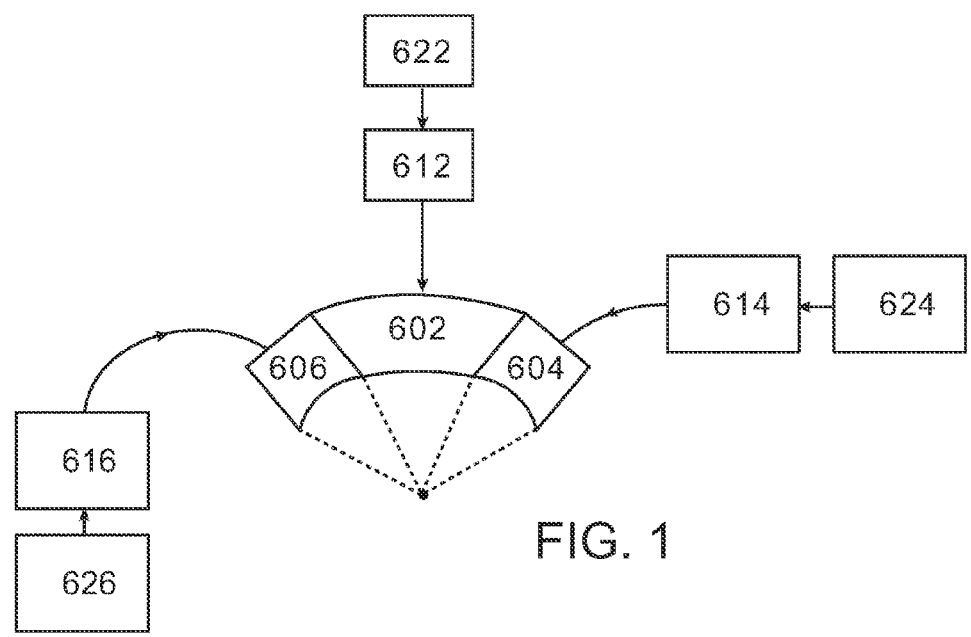
FIG. 1 illustrates a schematic of a split focus transducer.

The ultrasound transducer of the present invention may be either a fixed or variable amplitude ultrasound device. A computer is used to control a waveform generator or an amplifier. Signals from the waveform generator and amplifier control the operation of the transducer. A user can program the signal output from the waveform generator or the amplifier through the computer. Direct control of the waveform generator and amplifier are possible if the components have an independent control element. An imaging transducer can be utilized in conjunction with the high intensity focused ultrasound (HIFU) transducer. The imaging transducer may be a simple A-line transducer, or a more complex imaging device utilizing both a transmit and receive beamformer. Both the diagnostic and therapeutic transducers used in the present invention may range from a single fixed focus element to transducer arrays that are electronically steered to produce complex transmission patterns and results within a target tissue.

Similarly when we discuss the electronic medical instruments that are transducers, each medical instrument that produces ultrasound and has an independent electronic identity is a single transducer for the purposes of the present invention. The restrictive definition provided does not apply when discussing transducers of the prior art. The definition is necessary to distinguish multiple transducers used together as described below. Furthermore, the description contains references to "elements" of a transducer, and transducer "sections." By "element" we refer to the diced partitions from a single die used by a transducer. Each "element" is controlled either individually or in a group by a beam former, signal generator or simple amplifier. In contrast a "section" refers to one or more elements operating as a single transducer. While it is theoretically possible in a phased array to utilize a single transducer to produce multiple focal zones and wave forms simultaneously, the description of a "section" herein refers to a separately controlled transducer from another section, or a physically separate collection of elements. In this manner, multiple transducer sections can be controlled simultaneously to produce independent focal zones and/or wave forms.

In a first embodiment of the present invention there is an ultrasound transducer split into two or more equal size sections wherein each section has a discrete focal point. The transducer may be a hemispherical design or a flat annular array. The transducer is split into two halves or four quarters. Depending on the amount of energy that needs to be focused into the target area, the number of individual elements can be reduced and the number of partitions the transducer is split into can be increased. This with a fixed number of elements in a single transducer, the transducer can be split into as many partitions as needed or desired. Each partition then is shaped or steered to have a discrete focal zone different from each other section. The focal zones can be stacked on top of each other along the axis of the transducer, or distributed in a three dimensional volume in space before the transducer. In this way the energy from the transducer can be focused into several points at the same time.

Each time the split focus transducer emits ultrasound energy into tissue, the tissue will experience the desired ultrasound effect in more than one focal volume at a time. Depending on the shape of the transducer partitions, or the direction of the emission from each partition, a varying amount of depth can be treated, or a broader area at a single depth, or a combination of both.

During the manufacturing process for the transducer, the transducer can be made as a single focus transducer and then literally cut into partitions, then the partitions are rejoined so that the focal points of each section are distributed as desired. This requires sufficient capability to rejoin the transducer partitions at varying heights or angles to one other to produce the desired distribution of focal points.

In a second embodiment of the present invention there is a transducer assembly having a first focused ultrasound transducer operating at a first frequency and a second transducer operation at a second frequency. During use the first transducer emits focused ultrasound energy and produces cavitation within a focal region. Micro bubbles form in the adipose tissue in response to the first transducer, and the frequency of ultrasound generated. The second transducer operates at a lower frequency and is broadcast into the patient's tissue either in focused manner or unfocused. If focused the second transducer has a focal region that overlaps the focal region of the first transducer. The focal region of the second transducer may be larger than the focal region of the first transducer so as to provide a certain safety margin for the overlapping volume of the first transducer. The frequency of the second transducer is designed to cause the collapse of the bubbles produced by the first transducer. In this way the first transducer may be fired into a patient in either pulsed or continuous mode, and as soon as bubbles are formed the second transducer forces them to collapse.

The collapse of the bubbles produces micro volumes of extreme heat dissipation at the moment of collapse of each bubble. The result is that the bubbles created in a certain volume of tissue will release sufficient energy to perform heating necrosis of the local cell population. Yet because the heating occurs from micro bubble collapsing and not from thermal transfer using the ultrasound transducer, there is no danger of burning the patient's skin because of a hot transducer, or over heating the local volume of tissue to produce the desired results. Thus the heating necrosis is done in an extremely short interval of time instead of the traditional longer period of time required with simply heating the tissue to a desired temperature.

It has been known for some time that physically damaging effects from cavitation may be enhanced by actively causing the collapse of bubbles with a compression wave. Here bubbles are formed using the first transducer and collapsed with the second transducer. The first signal causing the bubbles to form is a high-frequency transducer (e.g. >1 MHz) wave that can be precisely positioned. The second transducer generates a collapsing wave by emitting low frequency ultrasound (e.g. <1 MHz). The low frequency ultrasound may be focused, or may be unfocused so the low frequency ultrasound floods the volume of space the high frequency transducer is focused on.

The high frequency transducer of the transducer assembly is driven by an electronically controllable signal generator. This provides for the delivery of 1 to 1000 watts of acoustic energy in either pulsed or continuous form. The low frequency transducer of the transducer assembly, may be focused or unfocused and is driven by and electronically controllable through a signal generator allowing the delivery of 1 to 1000 watts of acoustic energy in either pulsed or continuous form. The high frequency signal generator forms a high frequency subsystem, and is operated at high power. (e.g. greater than 100 watts) with short pulse durations (less than 100 ms). The low frequency signal generator forms the low frequency sub system and is preferably operated in pulse mode. The low frequency sub system preferably operates at higher power with short pulse durations to force the collapse of bubbles formed by the high frequency transducer. The intense energy release by the collapse of the bubbles damages the tissue to achieve the desired necrotic effect.

In another embodiment of the present invention there is an interchangeable electronic instrument assembly comprising three types of components. First a receptacle having a plurality of sockets. Second a plurality of electronic medical instruments that have a common style of electronic communication plug for engaging the plurality of sockets, each electronic medical instrument has an electronic identity. Third is a medical appliance in electronic communication with the receptacle and having at least one signal generator, a data I/O bus, and a power supply. The medical appliance can detect and identify each electronic medical instrument through the electronic communication plug when the instruments are engaged with the sockets. The medical appliance can control each electronic medical instrument according to a set of operation parameters.

This embodiment provides for an interchangeable device that can receive different medical instruments. The receptacle is shaped to have two or more sockets. The sockets are a uniform design to promote interchangeability of parts. The electronic medical instruments may be transducers, sensors (such as thermal, electrical or optical sensors), guides or testing instruments. Each instrument has a socket end and a free end. The socket ends of the medical instruments are uniform in design so they may be used interchangeably between the sockets. The electronic medical instruments each contain the necessary electronics to operate so long as they receive commands and power from the medical appliance. When the socket is engaged to the plug of each electronic medical instrument, the medical appliance queries each instrument plugged into the receptacle. The medical instruments respond to the query and identify themselves electronically to the medical appliance. The medical appliance then knows what combination of elements and capabilities are present in the receptacle.

Thus the affect of a split focus or multipoint focusing transducer can be achieved using a plurality of transducers as the electronic medical instruments. Each transducer having a different focal depth or different operating frequency is plugged into the receptacle. The medical appliance can determine automatically which transducers are present and control the therapeutic distribution of ultrasound automatically.

Multiple transducers designed to produce cavitation in adipose tissue can be used with the receptacle. In one alternative embodiment, a plurality of small transducers operating at different frequencies can be focused to a common focal point. The affect of the overlapping frequencies produces the desired cavitation through a beat frequency effect. Thus a first transducer may have a first frequency $X_1$, while a second transducer has a second frequency $X_2$. The combination of the two frequencies at the common focal point generates cavitation, and eliminates the danger of heat accumulation and burning on the surface of the patient. Additional frequency transducers can be employed so the bubble forming affect is further distributed out among more physical components constructed together with the receptacle. Using a split focus transducer as previously described in combination with a plurality of individual interchangeable instruments allows for multiple focal zones to be treated while retaining the advantage of non harmful energy being transmitted through the patient until the ultrasound beams converge at the desired focal zones.

In yet another embodiment, the interchangeable electronic medical instrument assembly may use a first imaging transducer to help a physician direct the ultrasound energy into adipose tissue, and a second therapeutic transducer to actually create cavitation in the adipose tissue. The second transducer may be supported by an additional transducer to provide for a high and low frequency combination effect, or use one or more split focus transducers to cover a larger volume of adipose tissue in a single pass.

Turning now to the drawings FIG. 1 provides a simple schematic of the present invention. A transducer assembly 600 is illustrated having three component transducers 602, 604, and 606. The three component transducers focus onto a single focal point 630. Each transducer has an amplifier 612, 614, and 616, respectively, and a frequency generator 622, 624, 626, respectively, associated with it. Although the illustration indicates there are three transducers with necessary electronics, the present invention is not limited to three. Additional transducers and focal zones in nearly any combination are possible as shown below.

Figure 2A:
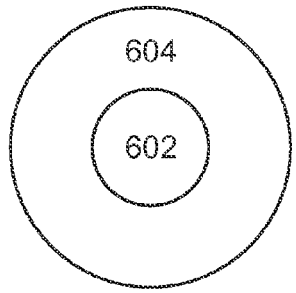
FIGS. 2A-D illustrate various split focus transducers having a common focal point.
Figure 2B:
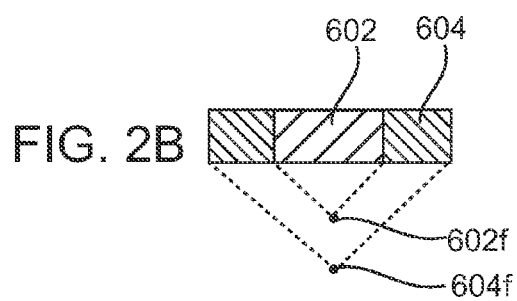

Alternative embodiments are illustrated in FIGS. 2A-2D. A first split focus flat ultrasound transducer, as illustrated in FIGS. 2A and 2B and has a center transducer 1602 and a annular ring transducer 1604. The first transducer 1602 focuses into a first focal point 1602$f$ while the annular ring transducer focuses on a second focal point 1604$f$. The frequencies of the two transducers are preferably different producing an interference effect at the focal zone. Other variations are permitted within the scope of the present invention as where the first transducer may be an imaging transducer and the annular ring may be a therapeutic device.

Figure 2C:
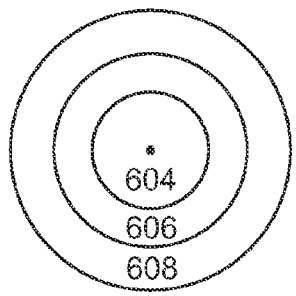
Figure 2D:
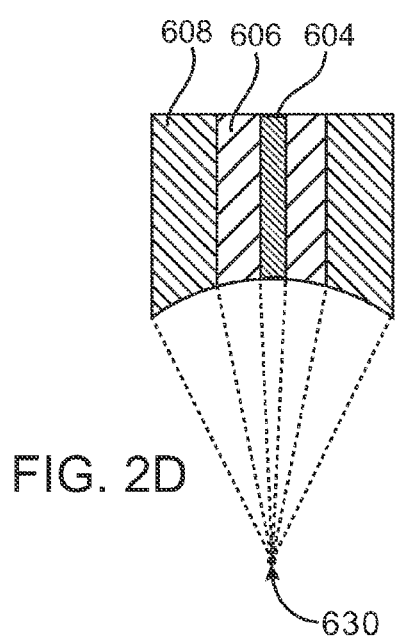

Furthermore the use of additional transducers frequencies and focal zones in a single assembly allow for a great deal of diversity in procedural outcomes. Three equal sized transducers in a single assembly are illustrated in FIGS. 2C and 2D. It can be seen here that though there are three partitions of approximately the same area, they need not be the same shape. This allows for a great complexity in signal interference to be produced at the focal zone. The signal interference allows lower energy signal emissions from the transducers to achieve the same result. In this manner the tissue along the emission path of each transducer is exposed to less dangerous radiant energy than using a transducer having a single frequency and amplitude. The transducer array of the present invention allows low energy zones culminating in a single effective focal area 1630 (FIG. 2D).

The various frequencies of the transducers 1602, 1604, and 1606 can be made to provide a therapeutic effect. For example the first transducer 1602 may be an imaging transducer allowing a physician to view the tissue where the focal point 630 is projected. The second transducer may be a high energy high frequency device intended to produce caviation in the tissue at the site of the focal zone. The third transducer may be a lower energy transducer, with a focal point or a broad focal range. The low frequency transducer would provide a sound wave to collapse the bubbles caused by the second transducer and produce micro pockets on sudden high temperatures that can cause cellular necrosis.

Figure 3A:
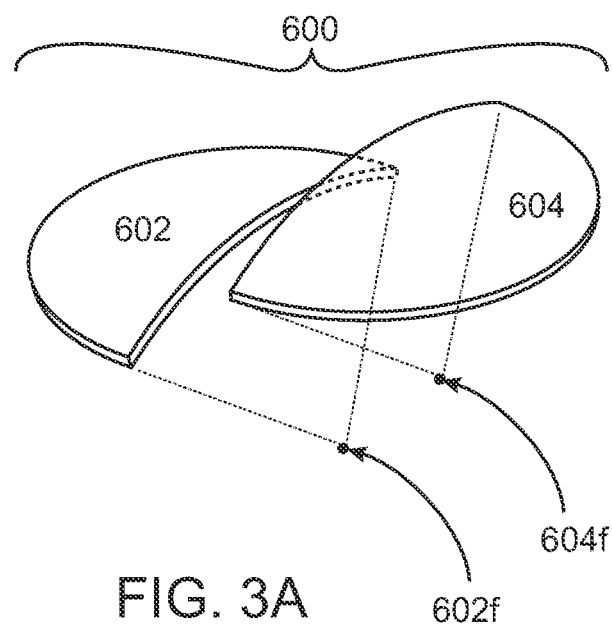
FIGS. 3A-D show a split focus transducer having two or more focal points.
Figure 3B:
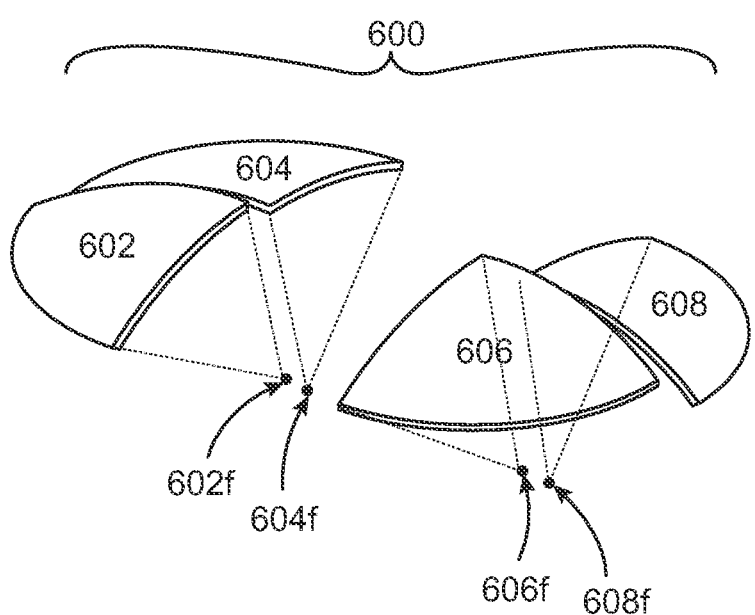
Figure 3C:
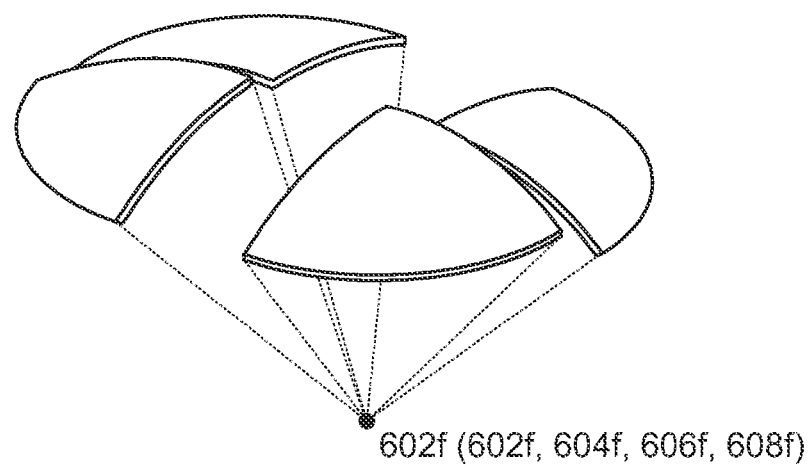
Figure 3D:
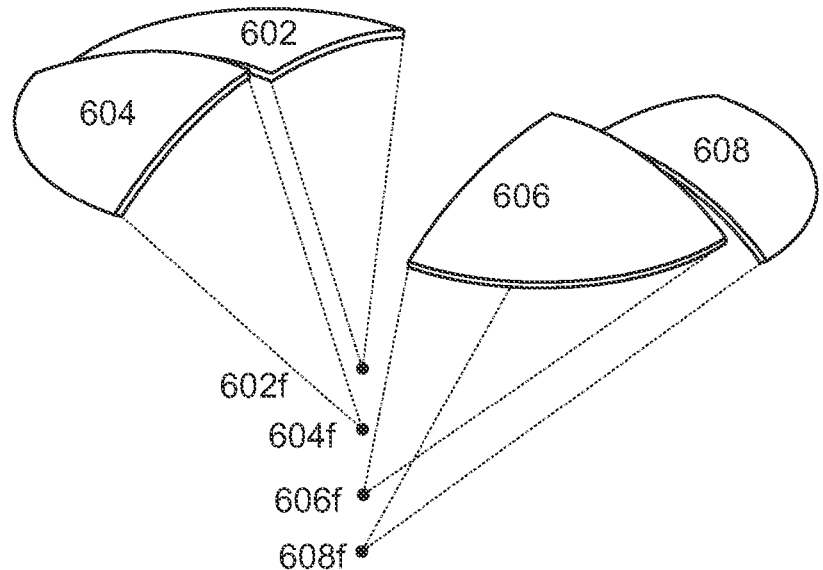

Alternatively, a split focus transducer 2600 (FIG. 3A) having two sections may be assembled into a single transducer which radiates energy into two discrete focal zones 2602$f$, and 2604$f$. The transducer assembly 3600 may be further sub divided into sections 3602, 3604, 3606, and 3608 to produce additional discrete focal zones 3602$f$, 3604$f$, 3606$f$, and 3608$f$ (FIG. 3B). The assembly 3600 can be used to project all the focal zones in a straight vertical axis (relative to the transducer face, FIG. 3C) or arranged to be spread out in a three dimensional pattern (FIG. 3D).

Figure 4A:
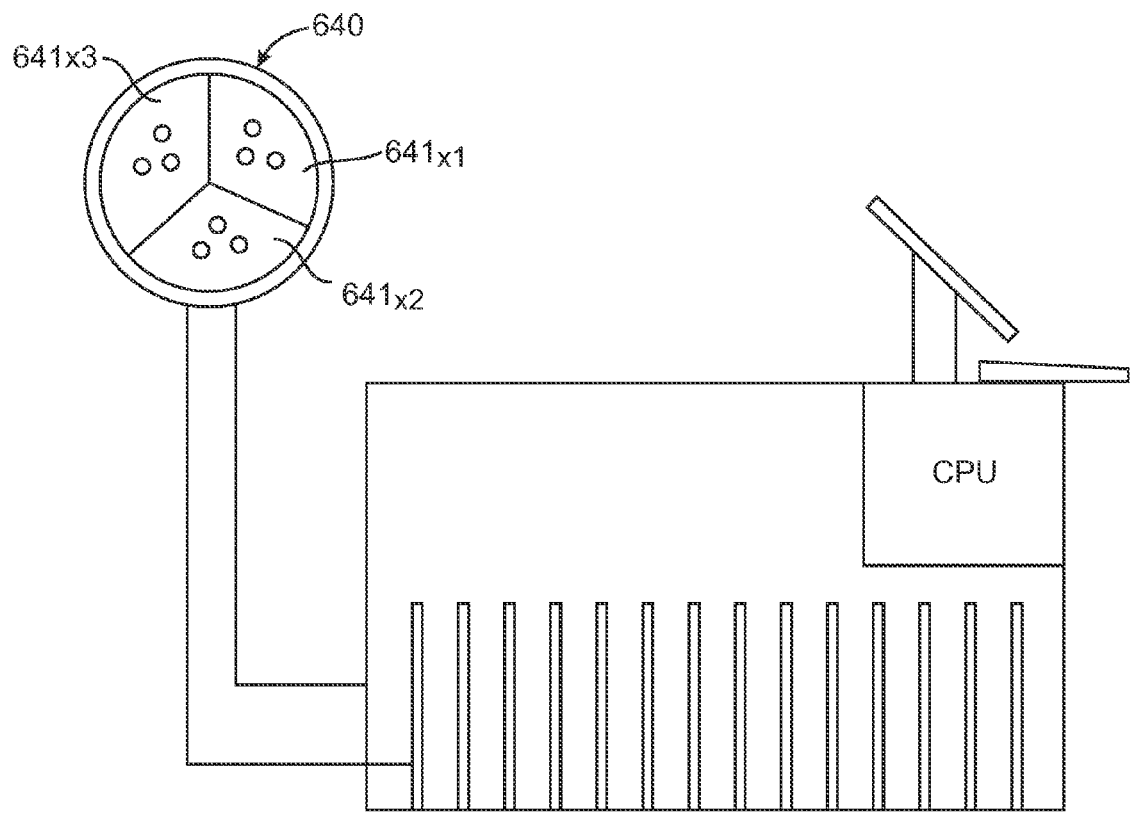
FIGS. 4A-C illustrate a system with a receptacle for a component transducer.
Figure 4B:
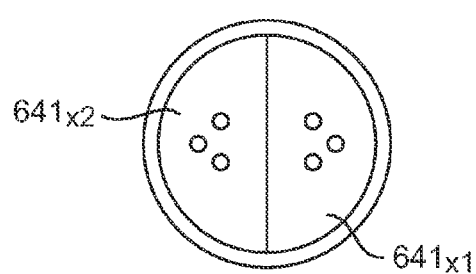
Figure 4C:
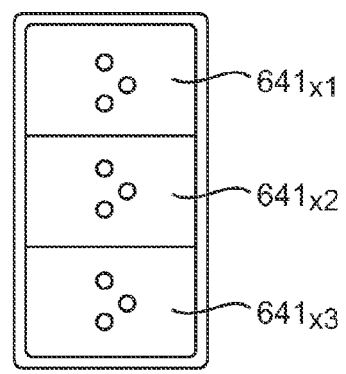
Figure 5A:
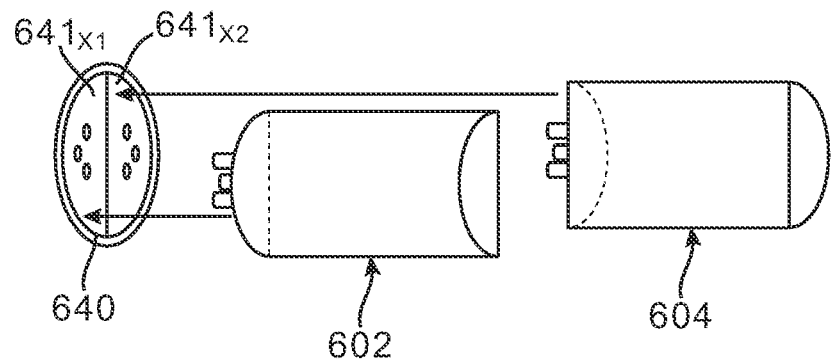
FIGS. 5A-B illustrate various receptacle and component types.
Figure 5B:
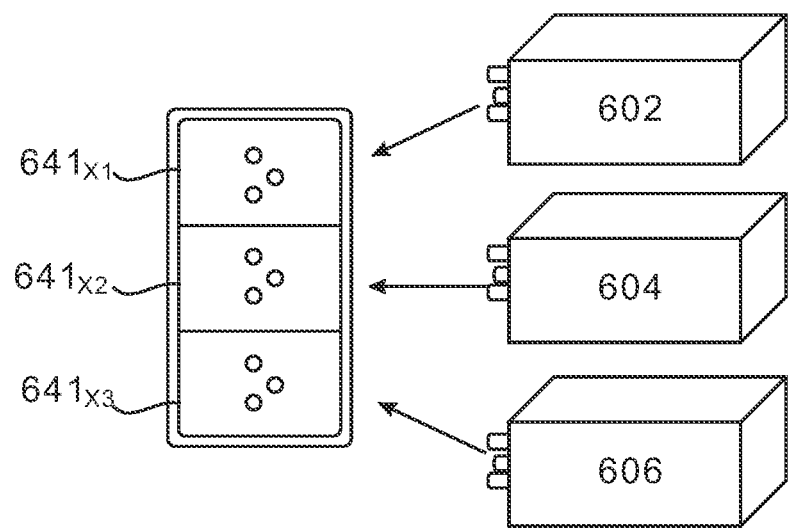

A single split focus transducer still has the limitations of not being adaptive for a variety of medical procedures "on the fly." An adaptive HIFU device (FIGS. 4A-C) has receptacle 640 having two or more sockets 641$x$1-$xn$. The sockets within the receptacle are uniform in size and shape allowing each socket to receive any medical device having the corresponding plug (FIGS. 5A-5B) for the socket type. The receptacle is connected to a medical appliance 400 having a processor and a set of programs for controlling the HIFU devices once they are installed into the receptacle. Each of these modular medical devices can be fit into the sockets, and are easily removable. Preferably the interchangeable transducer elements 602, 604, 606 can engage the socket in a manner that the transducer elements are stable and firmly seated within the sockets during use. However they are easily removable by having an operator pull them out when desired. Each transducer element 602, 604, 606 contains an identifying chip or circuit element. The identifying chip allows the medical appliance to query each of the interchangeable transducer elements as soon as the element is plugged into a socket. The transducer element identifies itself in response to the query with a response code. The response code can be used in a look up table that provides the medical appliance with the information about the transducer element (such as frequency, focal depth, amplitude, and the like). The medical appliance can now use the information from each of the interchangeable elements to identify what the combination of transducer elements is capable of. This allows the interchangeable transducer elements, and the medical appliance to serve as a split focus transducer with varying depths or focal regions. It further allows the transducer elements to be changed at any time to adapt the transducer to a wide range of therapy conditions and requirements.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:
1. A medical ultrasound system comprising:
a transducer assembly including a first focused ultrasound transducer configured to operate at a first frequency above 1 MHz and a second ultrasound transducer configured to operate at a second frequency below 1 MHz;
a first signal generator coupled with the first focused ultrasound transducer, the first signal generator configured to cause the first focused ultrasound transducer to operate between 100-1000 watts with pulse durations less than 100 ms; and a second signal generator coupled with the second ultrasound transducer, the second signal generator driving said second ultrasound transducer in pulse mode, wherein the first focused ultrasound transducer and the second ultrasound transducer are configured to be simultaneously operated so the first focused ultrasound transducer creates bubbles by projecting ultrasound energy at the first frequency into adipose tissue and the second transducer causes the bubbles to collapse by projecting pulsed ultrasound energy at the second frequency into the adipose tissue.

2. The medical ultrasound system of claim 1, wherein the second transducer is focused.

3. The medical ultrasound system of claim 2 wherein the first focused ultrasound transducer has a first focal region, and the second ultrasound transducer has a second focal region that is larger than the first focal region.

4. The medical ultrasound system of claim 1, wherein the second transducer is unfocused.

5. The medical ultrasound system of claim 1, wherein the first focused ultrasound transducer and the second ultrasound transducer comprise a split focus transducer.

6. The medical ultrasound system of claim 1, wherein the first focused ultrasound transducer comprises a first section of a split focus transducer and the second ultrasound transducer comprises a second section of the split focus transducer.

7. The medical ultrasound system of claim 6, wherein the first section is a center transducer and the second section is an annular ring transducer arranged relative to the center transducer.

8. The medical ultrasound system of claim 6, wherein the first section is an annular ring transducer and the second section is a center transducer arranged relative to the annular transducer.

* * * * *